US011445934B2

United States Patent
Zhao et al.

(10) Patent No.: US 11,445,934 B2
(45) Date of Patent: Sep. 20, 2022

(54) SYSTEMS AND METHODS FOR INTRAOPERATIVE SEGMENTATION

(71) Applicant: Intuitive Surgical Operations, Inc., Sunnyvale, CA (US)

(72) Inventors: Tao Zhao, Sunnyvale, CA (US); Vincent Duindam, San Francisco, CA (US); Caitlin Q. Donhowe, Mountain View, CA (US); Timothy D. Soper, San Jose, CA (US); Federico Barbagli, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1215 days.

(21) Appl. No.: 15/329,676

(22) PCT Filed: Jul. 17, 2015

(86) PCT No.: PCT/US2015/040988
§ 371 (c)(1),
(2) Date: Jan. 27, 2017

(87) PCT Pub. No.: WO2016/018646
PCT Pub. Date: Feb. 4, 2016

(65) Prior Publication Data
US 2017/0209071 A1 Jul. 27, 2017

Related U.S. Application Data

(60) Provisional application No. 62/029,927, filed on Jul. 28, 2014.

(51) Int. Cl.
A61B 5/06 (2006.01)
A61B 1/00 (2006.01)
(Continued)

(52) U.S. Cl.
CPC ............ *A61B 5/06* (2013.01); *A61B 1/00006* (2013.01); *A61B 1/00147* (2013.01);
(Continued)

(58) Field of Classification Search
CPC ........... A61B 5/06; A61B 5/065; A61B 5/066; G06T 7/75; G06T 7/149;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

CN 102196768 A 9/2011
CN 102763138 A 10/2012
(Continued)

OTHER PUBLICATIONS

Extended European Search Report for Application No. EP15826987.8, dated May 3, 2018, 8 pages.
(Continued)

Primary Examiner — Carl H Layno
Assistant Examiner — Manolis Pahakis
(74) Attorney, Agent, or Firm — Haynes and Boone, LLP

(57) ABSTRACT

A system comprises a medical instrument, including a sensing tool, and a processing unit configured to apply a segmentation function using a first seed to a three-dimensional image of a patient anatomy to create a model; receive position data from the instrument while navigating the patient anatomy; register a position of the instrument with the model; receive data related to the patient anatomy from the sensing tool; and update the model in response to detecting a difference between the model and the patient anatomy. Updating the model includes reapplying the seg-
(Continued)

mentation function using a second seed corresponding to a passageway of the patient anatomy that is not present within the model. Detecting the difference between the model and the patient anatomy includes analyzing temporal information obtained from shape data generated by the sensing tool while the instrument traverses portions of the patient anatomy not represented by the model.

27 Claims, 10 Drawing Sheets

(51) Int. Cl.
- A61B 34/20 (2016.01)
- G06T 7/73 (2017.01)
- G06T 7/149 (2017.01)
- G06T 7/50 (2017.01)
- G06T 7/00 (2017.01)

(52) U.S. Cl.
CPC ............ *A61B 5/065* (2013.01); *A61B 5/066* (2013.01); *A61B 34/20* (2016.02); *G06T 7/149* (2017.01); *G06T 7/50* (2017.01); *G06T 7/75* (2017.01); *G06T 7/97* (2017.01); *A61B 5/062* (2013.01); *A61B 2034/2051* (2016.02); *A61B 2034/2061* (2016.02); *G06T 2207/10016* (2013.01); *G06T 2207/10068* (2013.01); *G06T 2207/30061* (2013.01)

(58) Field of Classification Search
CPC . G06T 2207/10016; G06T 2207/10068; G06T 2207/30061
USPC ......................................................... 600/424
See application file for complete search history.

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 7,930,065 | B2 | 4/2011 | Larkin et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 10,278,615 | B2 * | 5/2019 | Zhao ..................... A61B 34/20 |
| 2005/0182295 | A1 * | 8/2005 | Soper ................. A61B 1/00172 600/117 |
| 2005/0182319 | A1 | 8/2005 | Glossop |
| 2006/0013523 | A1 | 1/2006 | Childers et al. |
| 2006/0184016 | A1 * | 8/2006 | Glossop ............... A61B 1/2676 600/434 |
| 2006/0281971 | A1 | 12/2006 | Sauer et al. |
| 2007/0015997 | A1 | 1/2007 | Higgins et al. |
| 2007/0060799 | A1 * | 3/2007 | Lyon ....................... G06T 7/70 382/128 |
| 2008/0123927 | A1 * | 5/2008 | Miga ..................... A61B 90/36 382/131 |
| 2008/0171934 | A1 | 7/2008 | Greenan et al. |
| 2010/0249506 | A1 | 9/2010 | Prisco |
| 2011/0201915 | A1 | 8/2011 | Gogin et al. |
| 2012/0059248 | A1 * | 3/2012 | Holsing ................. A61B 5/062 600/424 |
| 2012/0289777 | A1 * | 11/2012 | Chopra ................. G06T 19/003 382/128 |
| 2013/0102891 | A1 * | 4/2013 | Binnekamp .............. A61B 6/02 600/7 |
| 2013/0109957 | A1 * | 5/2013 | 'T Hooft ............ G01D 5/35316 600/424 |
| 2013/0223702 | A1 * | 8/2013 | Holsing .................... A61B 6/12 382/128 |
| 2013/0231556 | A1 | 9/2013 | Holsing et al. |
| 2013/0293578 | A1 | 11/2013 | Leung |
| 2013/0303893 | A1 * | 11/2013 | Duindam ................. G06F 19/00 600/424 |
| 2013/0324833 | A1 * | 12/2013 | Barley ................... A61B 6/466 600/417 |
| 2014/0039306 | A1 * | 2/2014 | Klinder ................. G06T 19/003 600/424 |
| 2014/0193058 | A1 * | 7/2014 | Bharat ................. A61N 5/1049 382/131 |
| 2014/0243660 | A1 * | 8/2014 | Klinder .................... A61B 6/12 600/424 |
| 2014/0275985 | A1 * | 9/2014 | Walker ..................... A61B 6/12 606/130 |
| 2014/0343416 | A1 * | 11/2014 | Panescu ................. A61B 34/30 600/431 |
| 2015/0306426 | A1 * | 10/2015 | Dehghan Marvast ....................... A61N 5/1007 600/8 |
| 2016/0183910 | A1 * | 6/2016 | Tahmasebi Maraghoosh ............ A61M 27/00 600/459 |
| 2017/0301088 | A1 * | 10/2017 | Bharat ................... A61B 34/20 |

FOREIGN PATENT DOCUMENTS

| | | |
|---|---|---|
| CN | 103648361 A | 3/2014 |
| JP | 2002200030 A | 7/2002 |
| JP | 2009502398 A | 1/2009 |
| JP | 2010104427 A | 5/2010 |
| JP | 2013202313 A | 10/2013 |
| JP | 2014506171 A | 3/2014 |
| KR | 20100098055 A | 9/2010 |
| WO | WO-2008125910 A2 | 10/2008 |
| WO | WO-2010060039 A2 | 5/2010 |
| WO | WO-2012024686 A2 | 2/2012 |
| WO | WO-2012092016 A1 | 7/2012 |
| WO | WO-2012114224 A1 | 8/2012 |
| WO | WO-2012158324 A2 | 11/2012 |
| WO | WO-2015011935 A1 | 1/2015 |

OTHER PUBLICATIONS

International Preliminary Report on Patentability for Application No. PCT/US2015/040988, dated Feb. 9, 2017, 7 pages.
International Search Report and Written Opinion for Application No. PCT/US2015/040988, dated Oct. 21, 2015, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Dec. 29, 2017 for Chinese Application No. 201580049546.9 filed Jul. 17, 2015, 10 pages.
Office Action for Chinese Application No. 201910367566, dated Oct. 15, 2021, 11 pages.

* cited by examiner

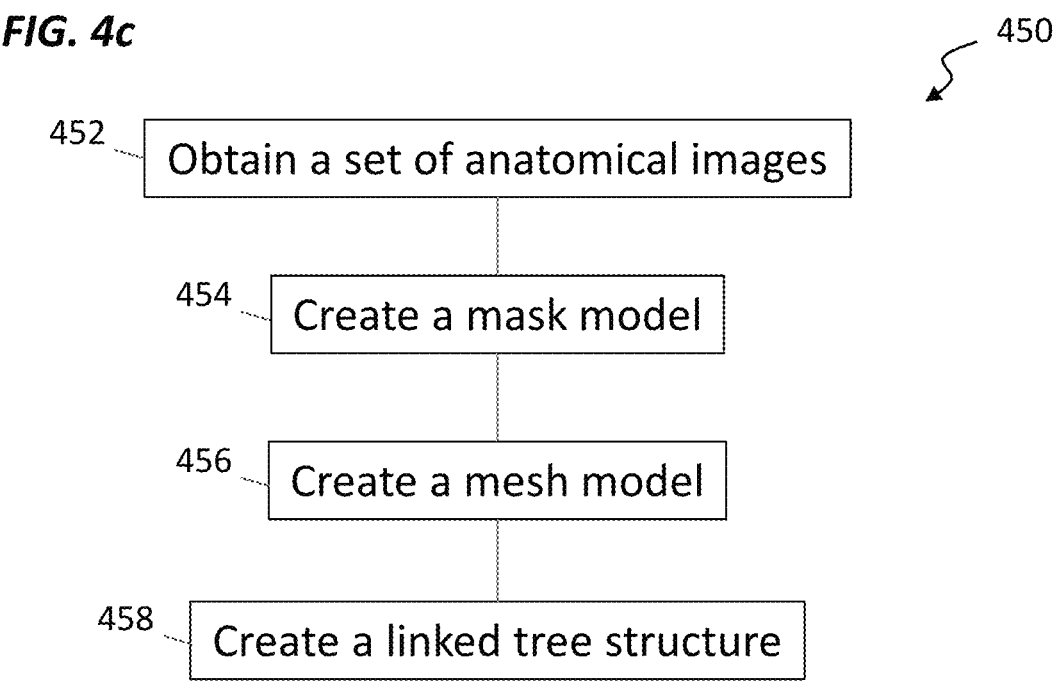

SYSTEMS AND METHODS FOR INTRAOPERATIVE SEGMENTATION

RELATED APPLICATIONS

This patent application is the U.S. national phase of International Application No. PCT/US2015/040988, filed Jul. 17, 2015, which designated the U.S. and claims priority to and the benefit of the filing date of U.S. Provisional Patent Application 62/029,927, titled "Systems and Methods for Intraoperative Segmentation," filed Jul. 28, 2014, which are all incorporated by reference herein in their entirety.

FIELD

The present disclosure is directed to systems and methods for creating models of a patient's anatomy using a process referred to as segmentation, and more particularly, to systems and methods for segmentation while navigating a patient's anatomy with a medical instrument.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

An image guided surgery process typically includes performing some type of pre-operative imaging of a target anatomy of a patient. For example, a Magnetic Resonance Imaging (MRI) image or a Computed Tomography (CT) image may be obtained. Through a manual and/or a computer software-based process, the images are partitioned into segments (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels.

Segmentation may be particularly useful in modeling anatomic passageways. After the segmentation process, the obtained model may be used to navigate a medical instrument through the segmented passageways of the patient anatomy. In some cases, various branches within the patient's anatomy may not be properly segmented by the segmentation process. For example, some passageways that exist within the patient anatomy may be omitted from the model. Or, the segmentation process may indicate the existence of branches where there are, in fact, none. Thus, a surgeon or an operator of the medical instrument who is using the model for navigation to a particular anatomic location may be hampered by inaccuracies in the model. To avoid such issues, it is desirable to have accurate segmentation capability.

SUMMARY

The embodiments of the invention are summarized by the claims that follow below.

In one embodiment, a method comprises navigating a patient's anatomy with a medical instrument, the instrument comprising a sensing tool. The method further includes correlating a position of the instrument with a model of the patient's anatomy. The method further includes, while navigating the patient's anatomy, updating the model based on data obtained by the sensing tool.

In another embodiment, a method includes for intraoperative segmentation includes, with a sensing tool of a medical instrument, obtaining data of a patient's anatomy while navigating through the anatomy. The method further includes comparing the data to a model of the patient's anatomy. The method further includes updating the model in response to determining that there is a difference between the model and the patient's anatomy as defined by the data.

In one embodiment, a computing system includes a processor and a memory comprising machine readable instructions that when executed by the processor, cause the system to apply a segmentation function to a three-dimensional image of a patient's anatomy to create a model, receive position data from a medical instrument while navigating the patient's anatomy, register a position of the instrument with the model, receive data related to the patient's anatomy from a sensing tool of the medical instrument, and update the model in response to detecting a difference between the model and the patient's anatomy.

In one embodiment, a method for intraoperative segmentation includes navigating a patient's anatomy with a medical instrument, the instrument comprising a sensing tool. The method further includes correlating a position of the instrument with a generic anatomy model. The method further includes, while navigating the patient's anatomy, updating the generic anatomy model to match the patient's anatomy based on data obtained by the sensing tool.

In one embodiment, a method for intraoperative segmentation includes navigating a patient's anatomy with a medical instrument, the instrument comprising a sensing tool. The method further includes, while navigating the patient's anatomy, using the sensing tool to obtain data related to the patient's anatomy. The method further includes constructing a model of the patient's anatomy in real time based on the data. The method further includes correlating a position of the instrument with the model.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4C is a flowchart showing an illustrative method for anatomic segmentation.

DETAILED DESCRIPTION

Figure 1:
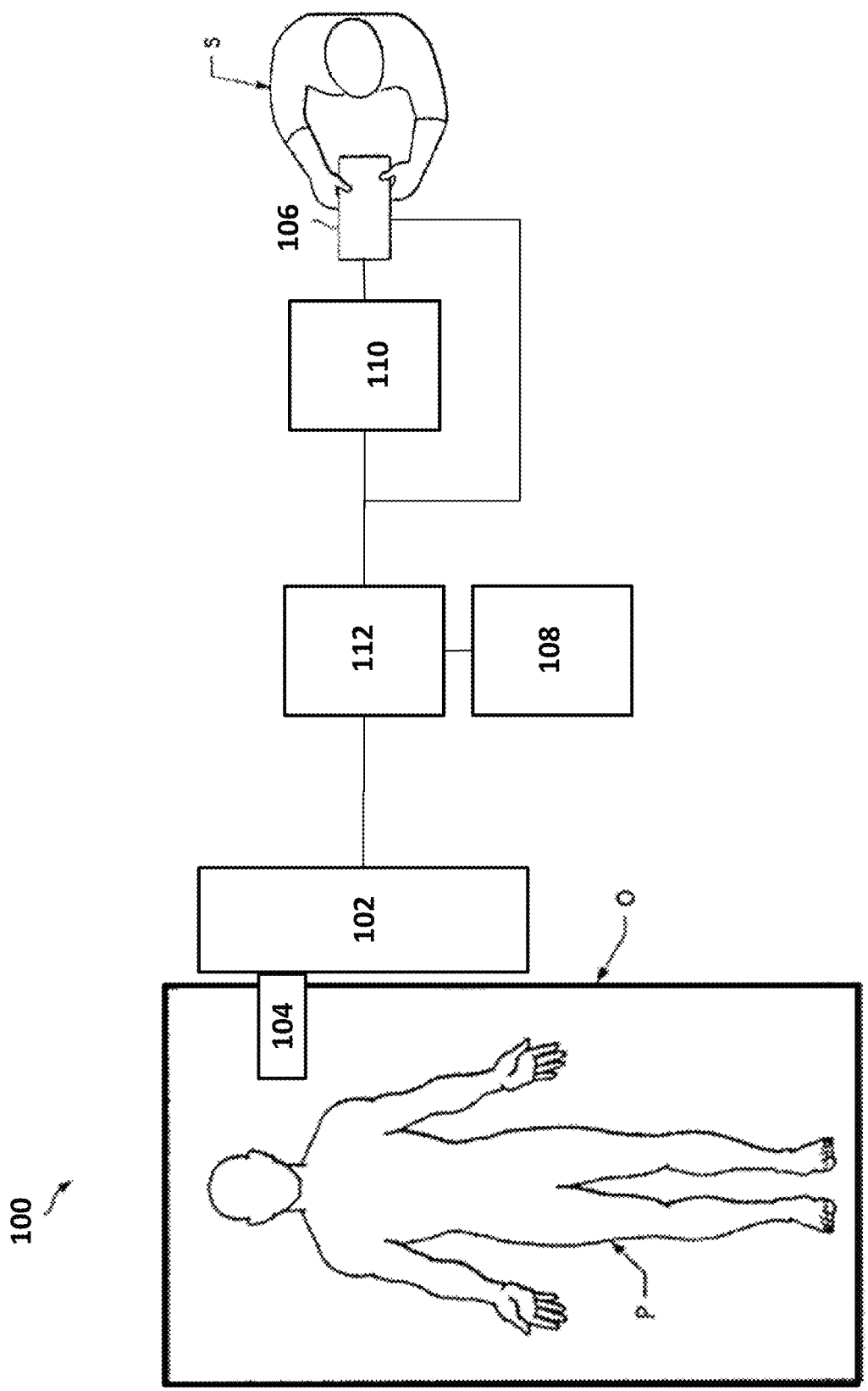
FIG. 1 is a diagram showing an illustrative teleoperational medical system, according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors.

The operator input system 106 may be located at a surgeon's console C, which is usually located in the same room as operating table O. However, it should be understood that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
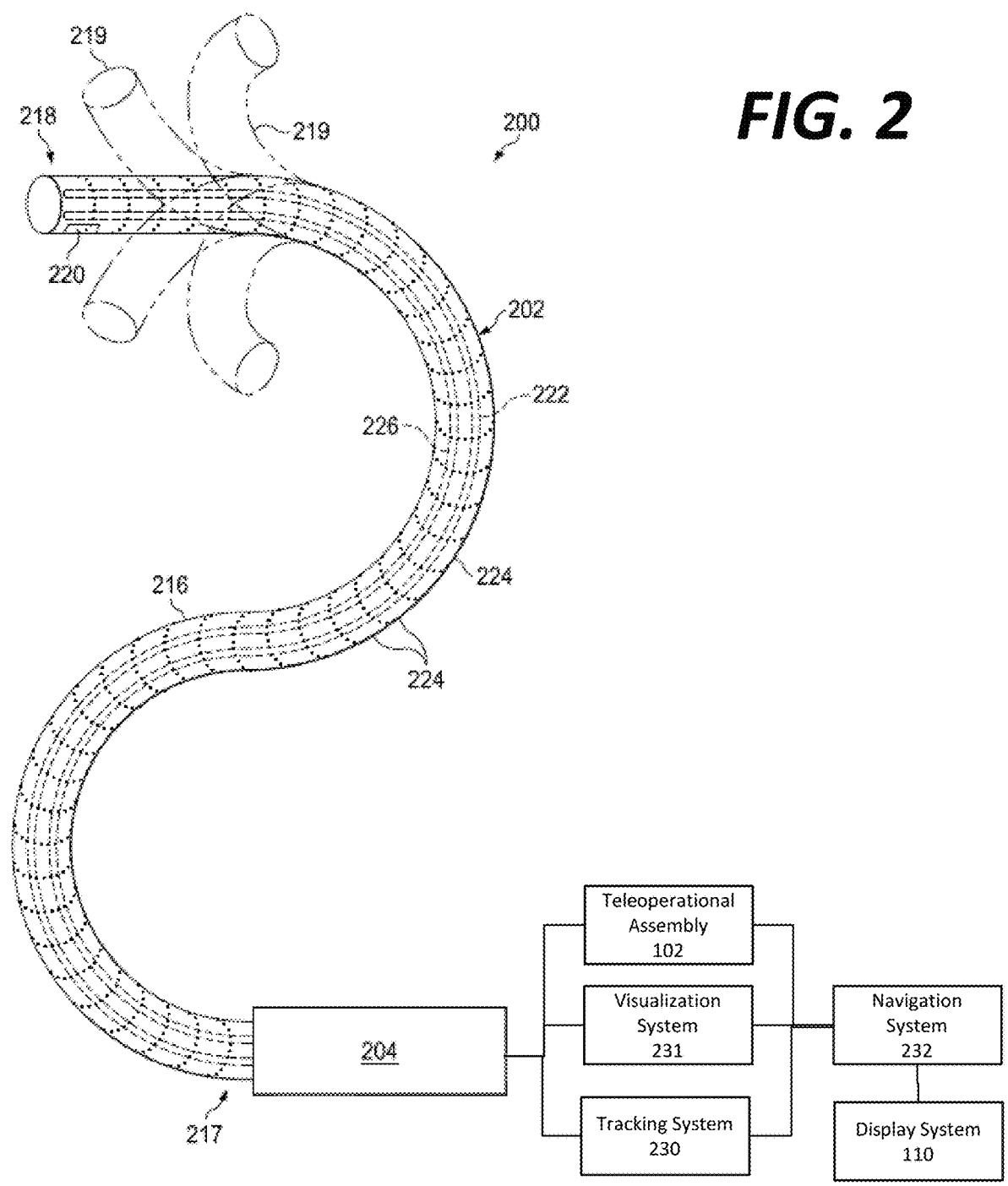
FIG. 2 is a diagram showing an illustrative medical instrument system comprising an endoscopic visualization system, according to one example of principles described herein.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary, or each core may be contained in a separate optical fiber.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths and therefore reflect only this narrow band of wavelengths while passing through a much broader band. During fabrication of the FBGs, the modulations are spaced by a known distance, thereby causing reflection of a known band of wavelengths. When a strain is induced on the fiber core, however, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065 (filed Jul. 20, 2006) (disclosing "Robotic Surgery System Including Position Sensors Using Fiber Bragg Gratings"), which is incorporated by reference herein in its entirety. The optical fiber may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

Figure 3A:
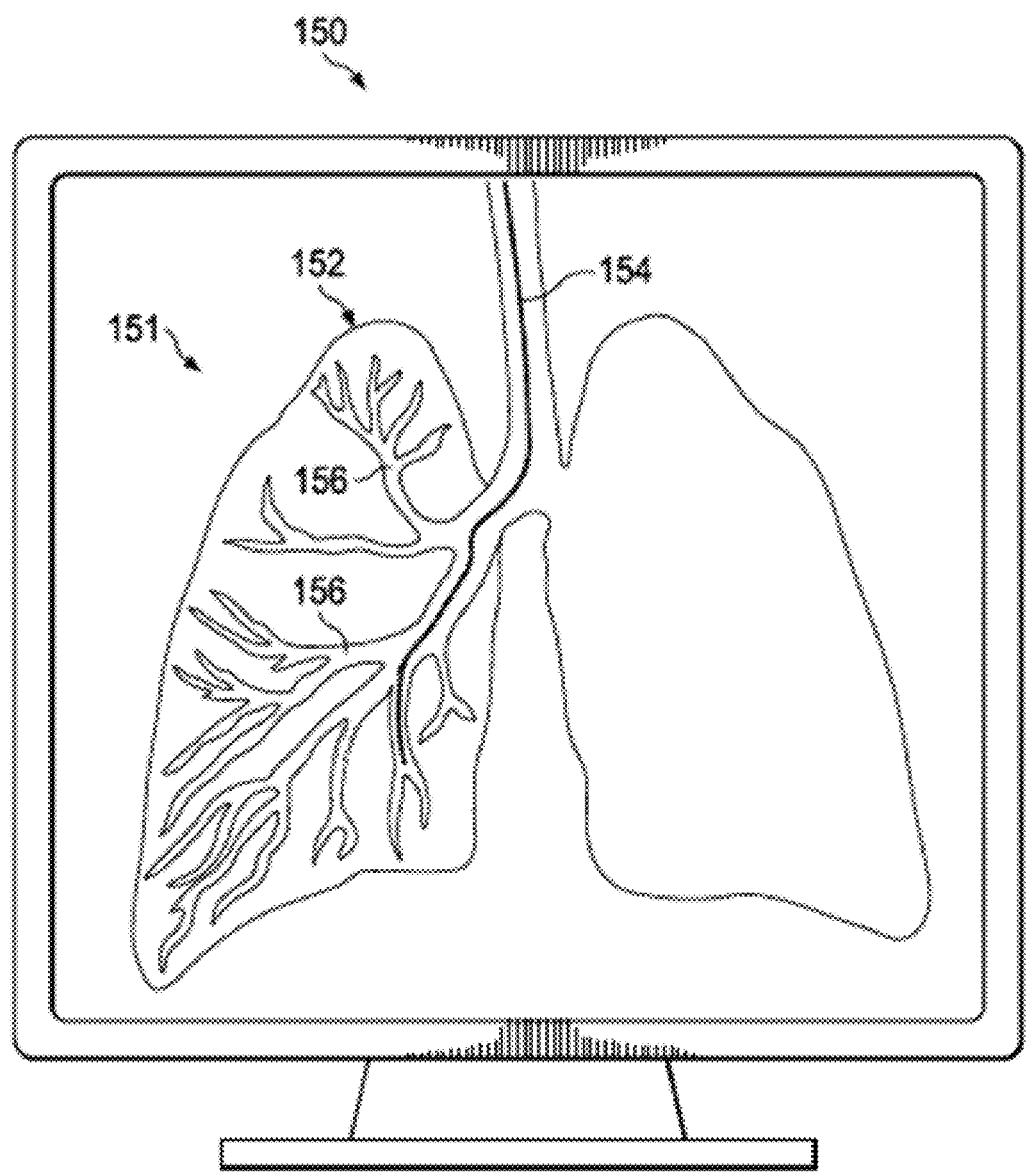
FIG. 3A is a diagram showing a model patient anatomy, according to one example of principles described herein.

FIG. 3A depicts a composite image 150 including a model 151 of a human lung 152, from a viewpoint external to the lung. The model lung 151 is registered with an instrument image 154 of a flexible instrument, such as catheter system 202. The model 151 of the lung 152 may be generated from a set of scanned images (e.g., pre-operative CT or MRI images) using a segmentation process. The composite image 150 may be displayed via display system 110. As the instrument is advanced through bronchial passageways 156 of the lung 152, information from the tracking system 230 and/or the visualization system 231 is used to register the instrument image 154 with the model lung image 151. The view of the model 151 of the lung 152 may change, for example, to depict the lung in a state of inspiration or expiration. The instrument image 154 may change to depict the advancement or withdrawal of the instrument through the bronchial passageways 156.

Figure 3B:
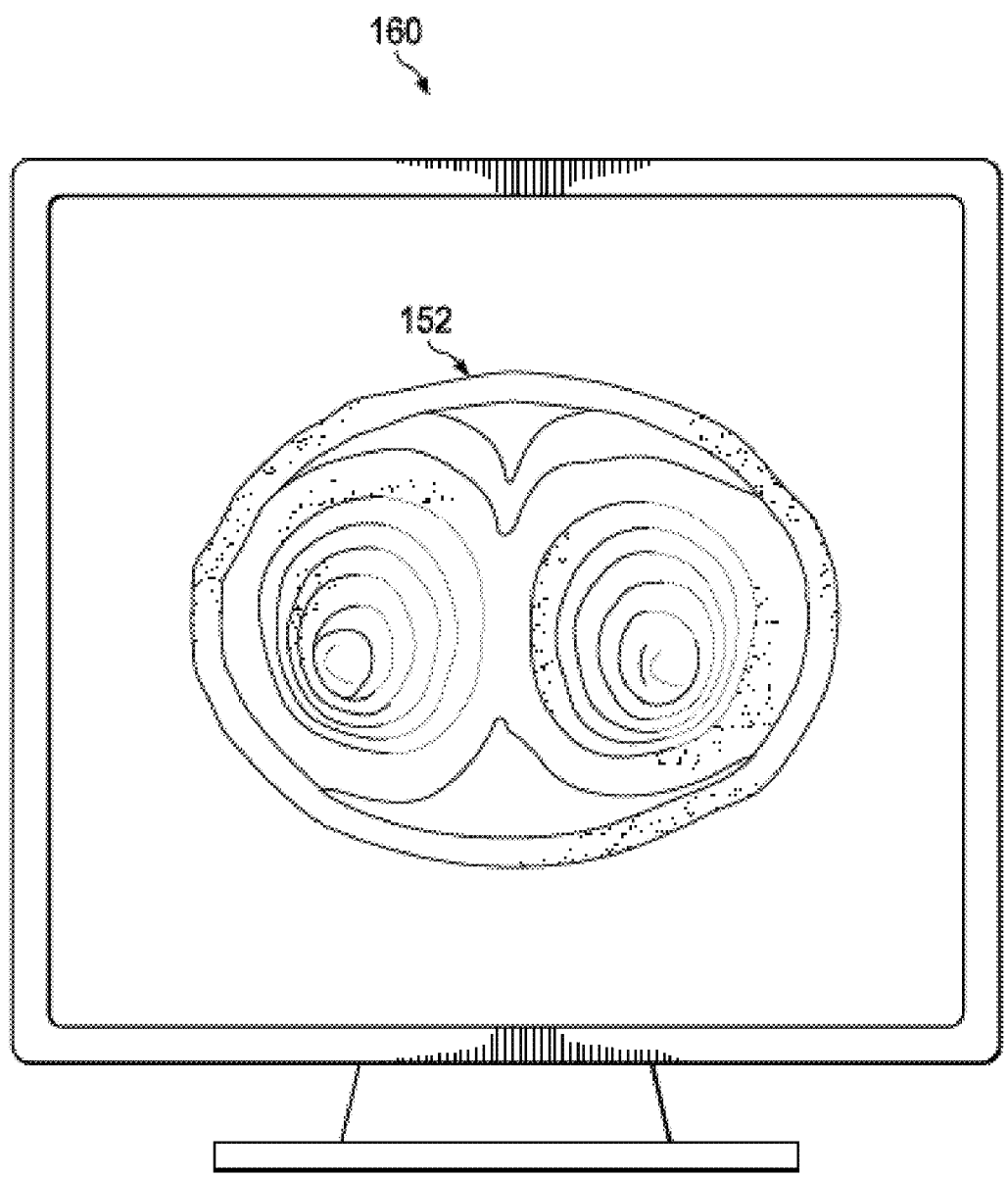
FIG. 3B is a diagram showing an image from an endoscopic instrument of a patient's anatomy, according to one example of principles described herein.

FIG. 3B is an internal image 160 of the human lung 152 depicting a region of the lung from the viewpoint of the instrument. The image 160 may be a concurrent image taken during the surgical procedure by the instrument while located in the depicted portion of the lung 152. More specifically, the image 160 may be captured by the visualization system 231. Alternatively, the image 160 may be a preoperatively recorded image selected based upon the location of the tip of the instrument 120 as determined by the tracking system 230.

Figure 4B:
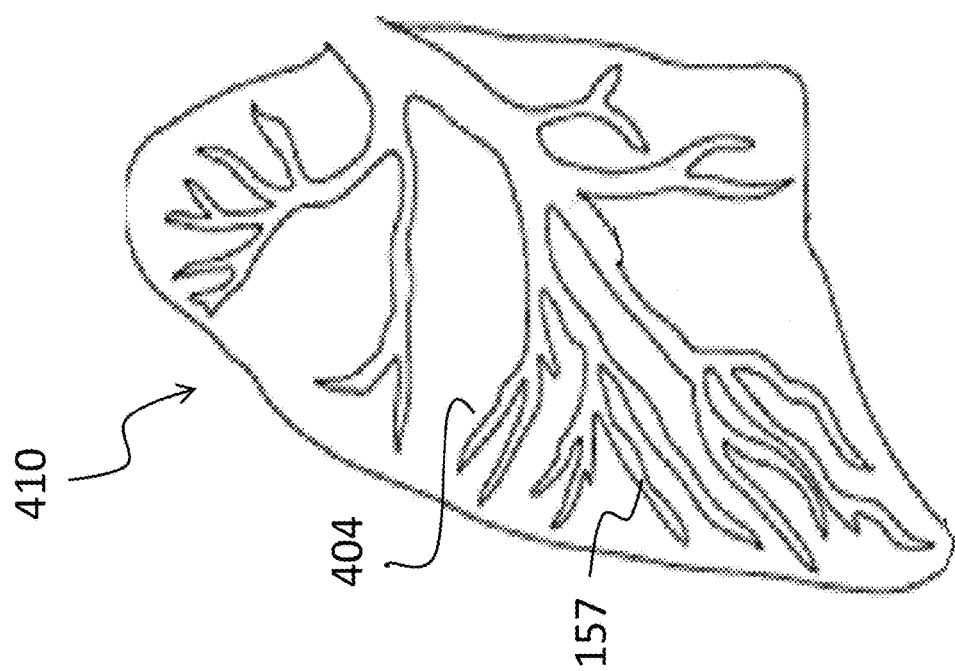
FIG. 4B is a diagram showing an illustrative model anatomy of the target anatomy, according to one example of principles described herein.
Figure 4A:
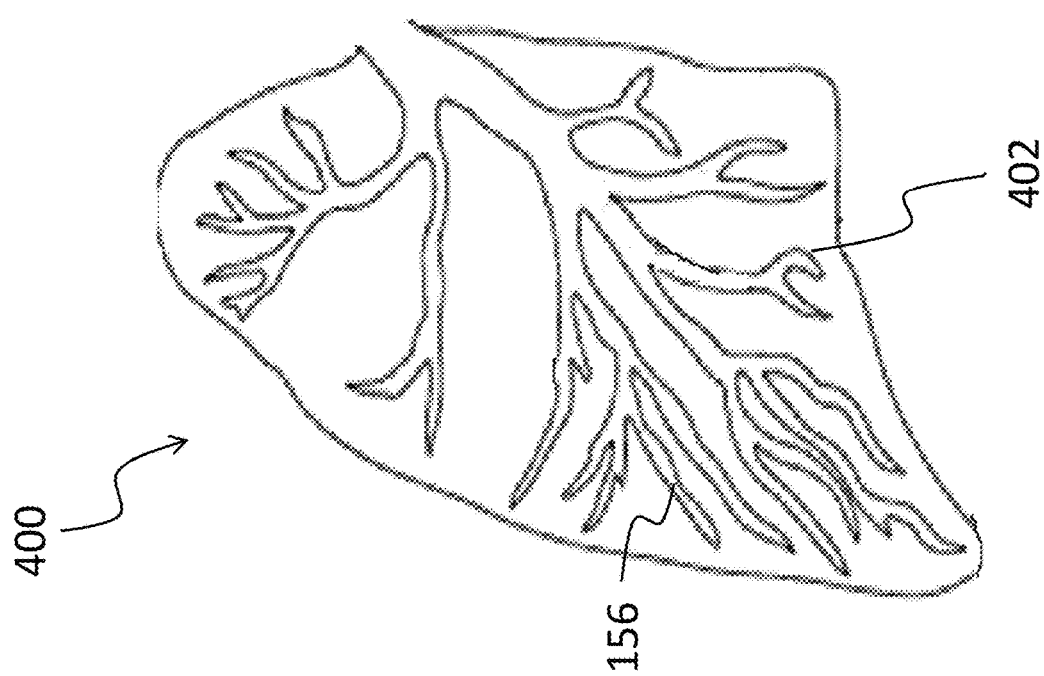
FIG. 4A is a diagram showing an illustrative target anatomy, according to one example of principles described herein.

FIG. 4A is a diagram showing an illustrative target anatomy 400, particularly, a patient's lung. The anatomy 400 represents the actual patient's lung, including all real branches and bronchial passages 156. FIG. 4B is a diagram showing an illustrative model anatomy 410 of the target anatomy. The model 410 is created through a segmentation process in which a composite of the scanned images is partitioned into segments (e.g., pixels or voxels) that share certain characteristics or computed properties such as color, intensity, and texture. This segmentation process results in a two- or three-dimensional reconstruction that forms the model 410. To represent the model, the segmentation process may delineate sets of voxels representing the target anatomy and then apply a function, such as marching cube function, to obtain a 3D surface that encloses the voxels. In some examples, volumetric rendering can be used to display the three dimensional volumetric data directly without use of a segmentation function. This can also potentially be used to display a probabilistic segmentation result. For example, the value of a mask can be assigned a number between 0 and 1, indicating a probabilistic result.

In one particular example, as shown in FIG. 4C, a segmentation method 450 includes a process 452 of obtaining a set of anatomical images such as from a patient CT or MRI scan. At a process 454, a mask model is created from the three-dimensional compilation of the set of anatomical images. For example, the anatomical passageways may be distinguished from surrounding tissue by assigning a first value (e.g., 1) to the airways and a second value (e.g., 0) to the surrounding tissue. If a particular region cannot be definitively determined to be a passageway or a region of surrounding tissue, a probabilistic value (e.g., something other than a 1 or 0) may be assigned to the indeterminate region. At a process 456, a mesh model may be created of the segmented passageways. Further details of the creation of a mesh model are described in detail in U.S. Provisional Patent Appl. No. 61/935,547 (filed on Feb. 4, 2014) (disclosing "Systems and Methods for Non-rigid Deformation of Tissue for Virtual Navigation of Interventional Tools") which is incorporated by reference herein in its entirety. At a process 458, a linked tree structure may be generated from the mesh model as described in further detail in U.S. Provisional Patent Appl. No. 61/935,547.

Ideally, the bronchial passages 157 within the model 410 will match the actual bronchial passages 156 of the patient anatomy 400. But, conventional segmentation processes used to create the model 410 may not create a model that accurately matches the actual anatomy. For example, the segmentation function may create a model having an additional passageway 404 that is not in the actual anatomy 400. In reliance upon this incorrect information, the clinician or an automated navigation system may plan a procedure that requires the medical instrument to navigate through or to the non-existent passageway to reach a target tissue. When the clinician reaches the location of the modeled passageway 404 and finds that, in fact, no passageway exists, the clinician may have to plan another approach to the target tissue. In some cases, the segmentation process may fail to render a passageway 402 that exists within the actual anatomy. In reliance upon this incorrect information, the clinician or an automated navigation system may not be able to plan the most effective route for a medical instrument to navigate to reach a target tissue.

Differences between the actual anatomy 400 and the model anatomy 410 may be discovered during a surgical operation while navigating a medical tool (e.g. the catheter 202 of medical instrument 200) through the passageway. As will be described in detail below, the differences between the actual and modeled anatomies may be detected by various imaging methods or by locating or attempting to locate the tool within a passageway. For example, while navigating the tool through the anatomy 400, the tool may capture images of and/or enter into an additional passageway (e.g., passageway 402) that is not in the model 410. Or, while navigating the patient's anatomy, the tool may approach an opening to a passageway (e.g., passageway 404) through which the catheter is intended to pass. Captured images or an inability to enter the passageway may indicate that the modeled passageway is missing. According to principles described herein, the model 410 can be updated to correct discrepancies between the model 410 and the actual anatomy 400.

Figure 5:
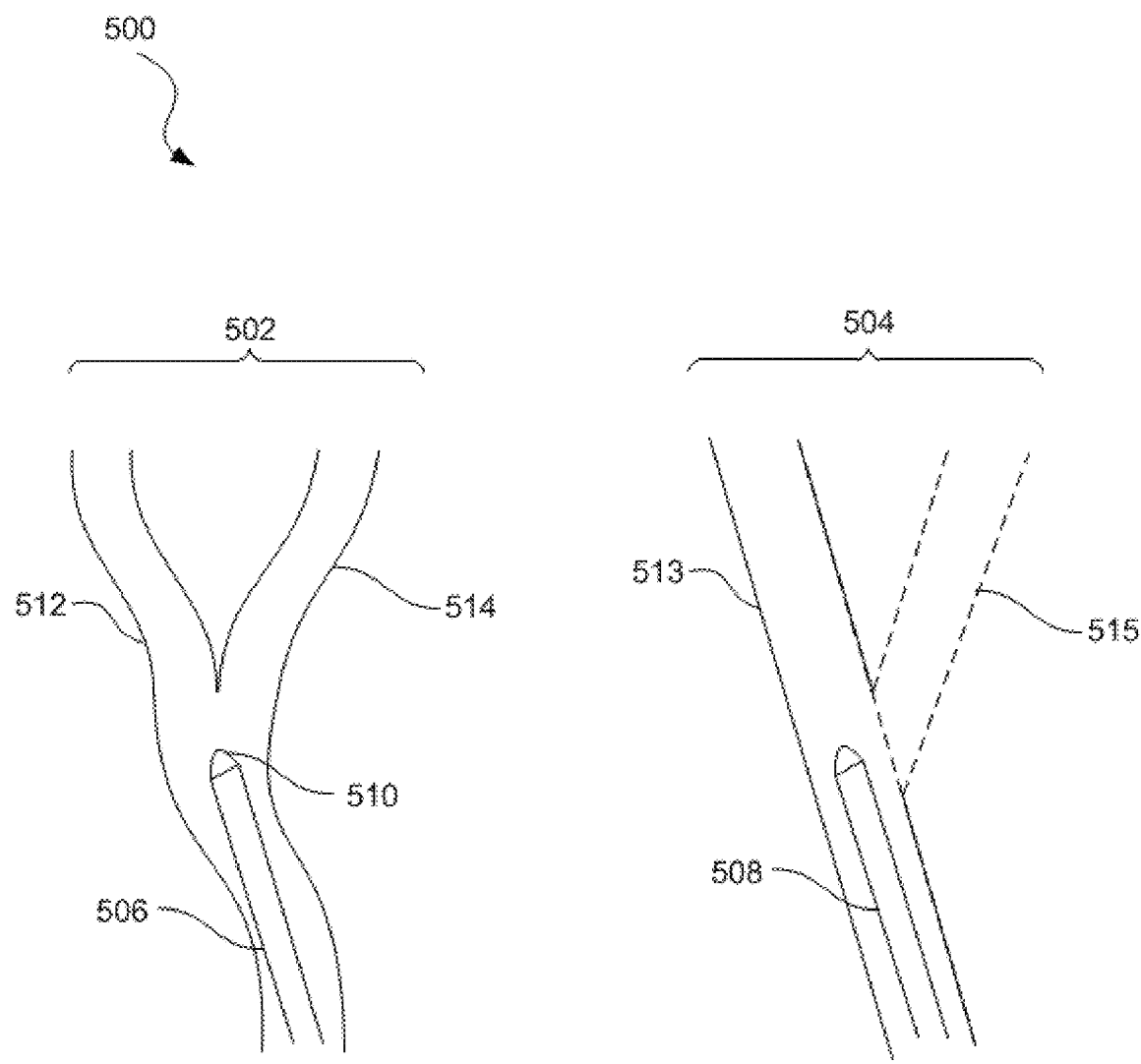
FIG. 5 is a diagram showing an intraoperative change to a model, according to one example of principles described herein.

FIG. 5 is a diagram 500 showing an intraoperative change to a model. FIG. 5 illustrates a real anatomy 502 and a model anatomy 504. According to the present example, as the medical instrument 506 navigates a passageway 512, a corresponding instrument image 508 is overlaid with the model 504. The model 504 includes a model main passageway 513 that corresponds with the real main passageway 512.

As the instrument 506 navigates the passageway 512, an additional branch 514 may be discovered. In this example, the additional branch 514 is not within the original model 504 that was created before inserting the instrument 506 into the passageway. The instrument 506 may include, at a distal portion of the instrument, a sensor 510 (e.g., an imaging system or a position detection system) that is able to determine, through one of a variety of methods described below, that there is an additional branch 514 that is not on the model 504. The dotted lines represent a new branch 515 within the model that corresponds to the additional branch 514 within the real anatomy 502. The branch 515 is referred to as a new branch because it was not part of the original model 504. But, after being discovered, and after the model has been updated, the new branch 515 is present within the model. The process used to update the model may include reapplying the segmentation function with additional information as will be described in further detail below.

Figure 6A:
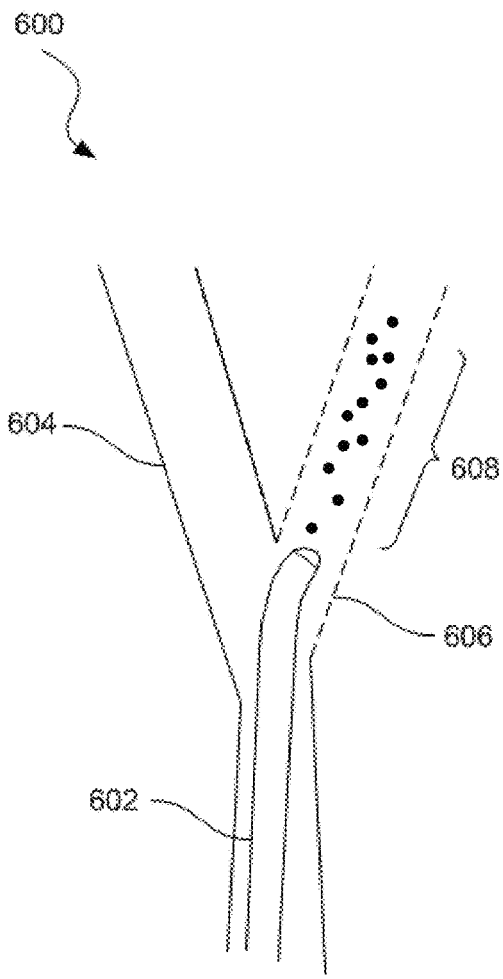
FIG. 6a is a diagram showing detection of an additional passageway for the model based on temporal position information, according to one example of principles described herein.
Figure 6B:
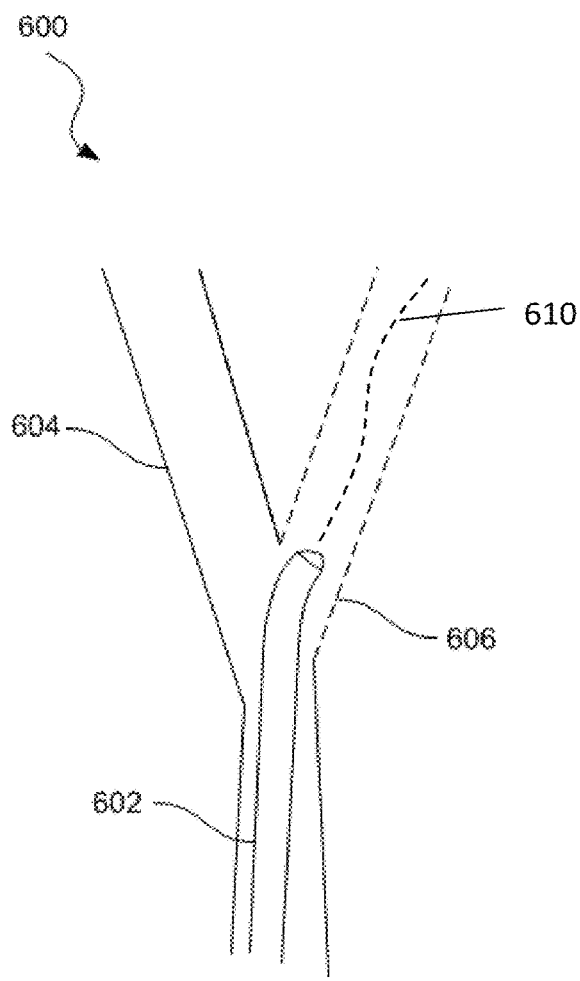
FIG. 6b is a diagram showing detection of an additional passageway for the model based on spatial position information, according to one example of principles described herein.

FIG. 6a is a diagram showing detection of an additional passageway for the model based on temporally integrated position information. FIG. 6b is a diagram showing detection of an additional passageway for the model based on spatially integrated position information. According to the present example, a medical instrument 602, which may be similar to instrument 200 described above, navigates a patient's anatomy 600. The medical instrument 602 includes a sensor system (e.g., sensor system 108) for obtaining time-varying values for the position of the distal portion of the instrument or for obtaining spatial information about all or a section of the elongated portion of the instrument. If temporal or spatial data obtained from the medical instrument indicates that the instrument is within or has been within a passageway that is not indicated by the model, the model may be updated using the obtained data.

Temporal data may be obtained from one or more of several different types of position sensors carried by the medical instrument. These time-varying values for the position of the medical instrument (e.g., the distal end of the medical instrument) may be integrated to indicate a path traversed by the medical instrument. One type of position sensor that may be used in accordance with principles described herein is an EM position sensor. An EM position sensor utilizes an electric or magnetic field that is created around the patient. The EM position sensor is able to detect a position in space by measuring the electric field at a specific point. Alternatively the position sensor may be a fiber-optic shape sensor. A fiber-optic shape sensor includes an optical fiber disposed along the length of the catheter. The optical fiber includes gratings that affect an optical signal passed through the fiber such that the shape of the fiber can be determined based on that signal. Additionally, by knowing a fixed position of the fiber in relation to the patient's anatomy, and by knowing the shape of the fiber, the location of the tip of the fiber can be determined. Another type of position sensor that may be used is a fluoroscopy based position sensor. Such a sensor includes one or more markers that are easily detected by a fluoroscopic image. Alternatively the entire shape of the device has sufficient contrast to its surrounding so that the shape can be extracted from a fluoroscopy image. Thus, the fluoroscopy can be done without the use of markers. Thus, the time-varying position of these markers can be detected by taking a fluoroscopic image of the patient while instrument is positioned and moving within the patient. Based on the position of the markers, it can be determined where the instrument is and has been located. Other types of position sensors, including impedance based position sensors, radiofrequency based position sensors, radiation based position sensors, may also be used in accordance with principles described herein. Additionally, the position of the instrument over time may be determined from position estimates from captured images within the passageways.

FIG. 6a illustrates temporal information 608 obtained from the instrument 602 as the instrument navigates from a main passageway 604 and enters into an additional passageway 606 that is not within the original model. The temporal information 608 indicates the discrete positions of the instrument at successive time intervals. This data can indicate the presence of an additional branch. In some examples, the temporal information can be filtered to take into account any cyclical motion of the tool caused by cyclical motion of the patient's anatomy. For example, patient respiration may cause cyclical movement of the bronchial passageways through which the instrument is navigating.

Spatial data may be obtained from one or more of several different types of position sensors carried by the medical instrument. The spatial data provides the positions of several portions of the medical instrument at one time value. One type of spatial data sensor that may be used in accordance with the principles described herein is an optical fiber shape sensor that indicates the shape of the elongated instrument positioned within an anatomical passageway. Another type of spatial data sensor is a multiple positional sensor (e.g., EM sensor) positioned along the device. Another type of spatial data sensor may be a set of fluoroscopic markers carried at multiple locations on the medical instrument or the shape of the device seen in fluoroscopic images. Each image of the set of fluoroscopic markers provides an indication of the shape of the elongated instrument positioned within an anatomical passageway. The obtained spatial data may provide an indication of the existence and shape of the additional passageway 606. In some examples, the position sensor is a range sensor, which may include a laser range finder, a time of flight sensor, an OCT sensor, or a depth camera.

FIG. 6b illustrates spatial information 610 obtained from the instrument 602 as the instrument 602 navigates from the main passageway 604 and enters into the additional passageway 606 that is not within the original model. The spatial information 610 indicates the shape of the instrument or the location of a set of position data at one time value. This data can indicate the presence of an additional branch. In some examples, the spatial information can be filtered to take into account any cyclical motion of the tool caused by cyclical motion of the patient's anatomy. For example, patient respiration may cause cyclical movement of the bronchial passageways through which the instrument is navigating.

The temporal information 608 or spatial information 610 may be used to update the model in various ways. For example, the information 608, 610 may be used to add voxels directly to a segmentation mask and then generate a three dimensional surface from those voxels. In another example, the information 608, 610 may be used to add seeds to the segmentation algorithm that was used originally as a user would do manually. The seed locations indicate to the segmentation algorithm where openings to additional passageways are located within the anatomy. This can cause the segmentation algorithm to investigate a particular area from the original images in greater detail or with a different level of discrimination to generate a more accurate model.

Figure 7:
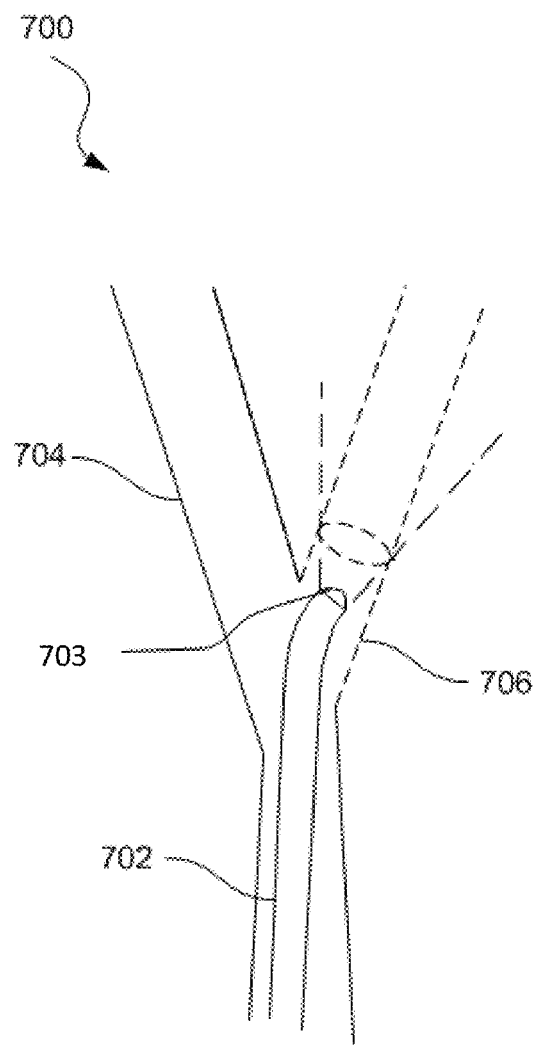
FIG. 7 is a diagram showing detection of an additional passageway for the model based on a set of acquired surface points, according to one example of principles described herein.

FIG. 7 is a diagram showing detection of an additional passageway for the model based on a set of acquired surface points. According to the present example, a medical instrument 702, which may be similar to instrument 200 described above, navigates a patient's anatomy 600. The medical instrument 702 includes a measurement apparatus 703 which may be a sensor (e.g. sensor system 108), a mechanical measuring device, and/or a component to enable the use of an external imaging system to provide measurement. The measurement apparatus 703 may be used to obtain two-dimensional or three-dimensional data about the environment around the sensor. The data may include data indicating surface tissue of a passageway 706 distal of the sensor. If the detected passageway 706 is not indicated by the model, the model may be updated using the obtained data.

Various imaging techniques may be used to acquire the real time information about the area around the distal end of the medical instrument. In one example, the measurement apparatus 703 is a time of flight camera mounted near the distal end of the instrument. A time of flight camera is a range imaging camera system that is able to measure distances based on the speed of light. Specifically, a time of flight camera measures the time-of-flight of a light signal between the camera and a particular surface to which distance is being measured. Thus, the time of flight camera can determine the distances between the measurement apparatus 703 and the inner surface of a passageway.

In one example, the measurement apparatus 703 may include one or more position sensors and a standard monoscopic endoscope camera that obtains a temporal series of localized two dimensional images of an illuminated anatomical area. These images can be combined with the monitored motion of the position sensors. Through use of the images and the tracked motion of the instrument, information about the three dimensional structures of the passageway 704 may be obtained. In one example, the position of the camera is determined from the image itself by using a structure from motion technique. Such a technique involves estimating three-dimensional structures from a sequence of two-dimensional images.

In one example, the measurement apparatus 703 may include an injection system and a fluid reservoir for injecting fluro-opaque dye into an area of interest within the anatomy. Then, multiple two-dimensional slices may be taken of the area where the dye was injected by a fluoroscopic imaging device external to the patient. In some cases, a rotational X-ray based imaging device may be used to take images of the area where the dye was injected. The dye provides a better contrast for the x-ray based imaging and thus provides more precise delineation of passageways through which the die flows. Three-dimensional structures can then be identified based on the two dimensional slices or the rotational images.

In one example, the measurement apparatus 703 includes a laser scanning device and one or more position sensors. The data from the laser scanning device about the detected anatomical points may be temporally integrated based upon the time-based location and orientation of the distal tip of the instrument. For example, an amplitude modulation scan (A-scan) may be taken from the tip of a fiber extending from the catheter. The information from the A-scan may be temporally integrated using position and orientation data from the tip of the instrument.

In one example, the measurement apparatus 703 may be a stereoscopic imaging system. A stereo endoscope produces two separate images from spatially displaced lenses. By correlating data from both images, three dimensional data can be constructed. Thus, the stereoscopic imaging system can determine the three dimensional surfaces around the distal end of the instrument 702. In one example, the measurement apparatus 703 may be a structured light imaging system. For example, a projector that has an offset in position projects light patterns that are seen by the camera. This information is used to reconstruct the 3D surface.

In one example, the measurement apparatus 703 may be an intravascular ultrasound (IVUS) system. An IVUS system can use ultrasound signals to measure the distance between the ultrasound transducer and surrounding tissue. An IVUS probe mounted on the tip of the instrument 702 can be used to scan the environment within a passageway to determine the three dimensional surface structures defining the passageway by projecting ultrasound signals in an axial direction. In one alternative example, the IVUS probe may be a forward facing probe. OCT, or Optical Coherence Tomography, is a technique to measure the fine tissue structure using an interferometer. It can also be used as a range finder to measure the 3D surface of the anatomical passage.

In one example, the measurement apparatus 703 may be a tool-based measurement device. For example, a biopsy needle may be extended to measure distances between the probe and various surfaces. Data from multiple measurements can be used to construct a three dimensional surface of the passageway through which the instrument is navigating.

The various types of data obtained using various types of measurement apparatus as described above may be used in a variety of manners to update the segmentation model. In one example, the obtained data may be in the form of a three dimensional point cloud. The three dimensional point cloud can be used to fit a triangular mesh or other three dimensional surface representation of the anatomy of interest. In some examples, the three dimensional data may be used to obtain voxels that can be added to a segmentation mask. This allows for a volumetric representation of the anatomy of interest. In some examples, the obtained data may be used to create seed points for the segmentation functions.

In some examples, the obtained data may be used to update the model in ways that do not involve an additional passageway. For example, the obtained data may indicate that a particular passageway is actually wider or narrower than indicated by the corresponding passageway in the model. For another example, spatial properties of the passages are changed for example to account for the changes to the model due to deformation. Thus, such obtained data may be used to make various changes to or fine-tune the model in real time during a medical procedure.

Figure 8:
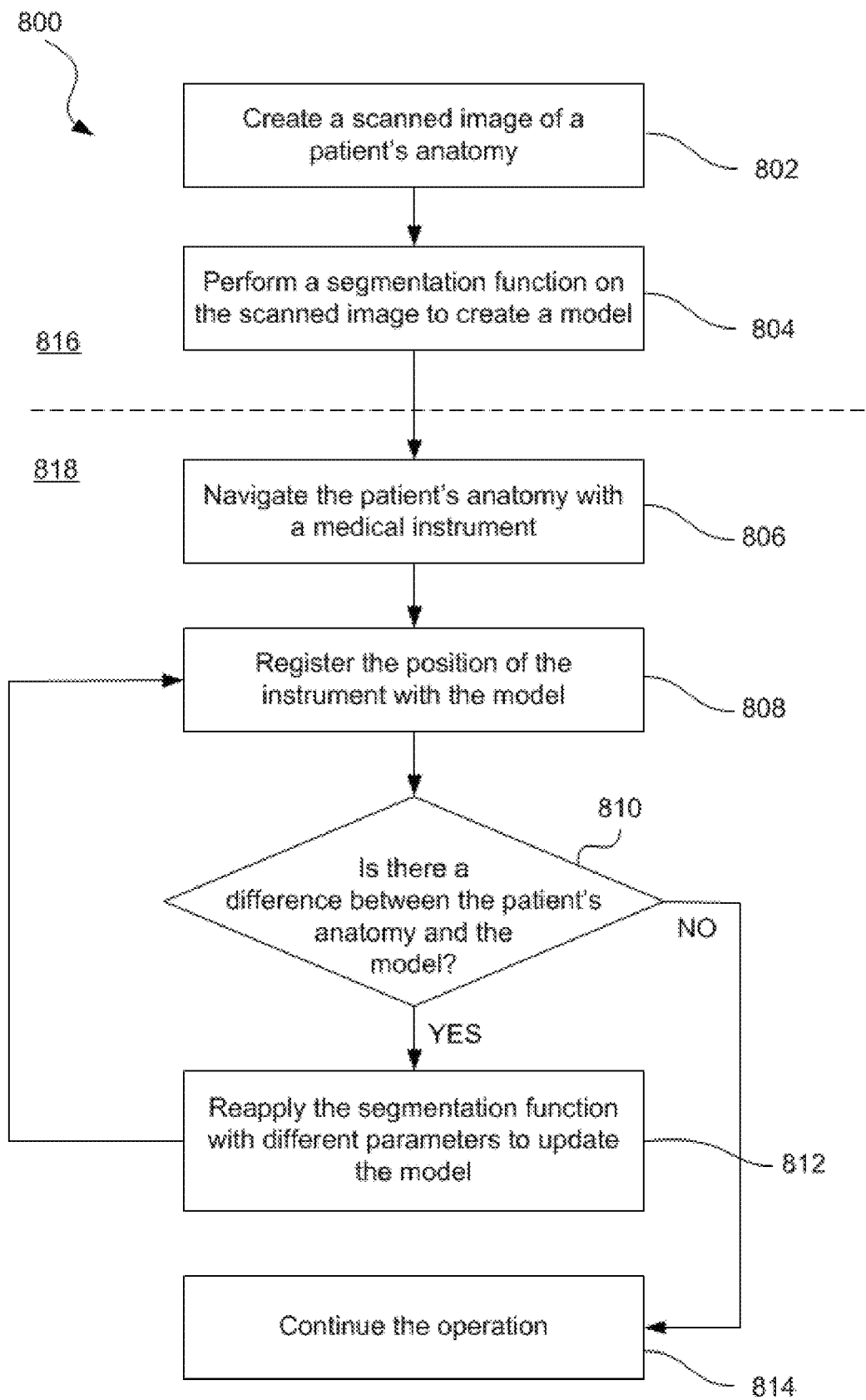
FIG. 8 is a flowchart showing an illustrative method for intraoperative segmentation, according to one example of principles described herein.

FIG. 8 is a flowchart showing an illustrative method for intraoperative segmentation. According to the present example, the method includes pre-operative processes 816 and intra-operative processes 818. For the pre-operative processes 816, the method 800 includes a process 802 for creating a scanned image of a patient's anatomy. This may be done through use of a variety of scanning mechanisms. For example, the scanned image may be done with a CT scan or an MRI scan. Other imaging systems are contemplated as well.

The method 800 further includes a process 804 for performing a segmentation function on the scanned image to create a model. Various segmentation functions may be used to create the model. The segmentation function may rely on a set of seed points selected by a user. Specifically, a clinician may review the scanned image and manually select seed points that indicate the opening of additional branches within the patient's anatomy.

In some examples, the segmentation function may assign probability values to potential airways found during the segmentation process. The airways having probability values above a threshold value can become part of the model. The airways having probability values below the threshold value may not become part of the model. But, the airways having probability values within a certain range below the threshold value may be used for adjusting the model as will be described in further detail below.

For the intra-operative process 818, the method includes a process 806 for navigating the patient's anatomy with a medical instrument. For example, if the end goal of the operation is to reach a target point to perform a lung biopsy, then the instrument may be guided along a pre-planned path to that target point. The process 800 further includes a process 808 for registering the position of the instrument with the model. Thus, as the instrument navigates through the patient's anatomy, an image of the instrument moves with respect to the model in a corresponding manner.

The method 800 further includes a process 810 for determining if there is a difference between the patient's anatomy and the model. This may be done through one of the methods described above. For example, the instrument may include a sensor to obtain spatial and temporal data or the instrument may obtain measurements used to construct a three dimensional surface of the interior of the anatomy. Using such data it can be determined if the actual anatomy matches the model. In some cases, multiple anatomical features may be analyzed. For example, both airways and arteries within a lung may be compared with the model to determine any differences. Additionally, in some cases, user input may help determine if there is a difference between the actual patient's anatomy and the model. For example, a surgeon may be able to visually determine that an artery or airway as viewed from a camera or a CT image is different than the model. The surgeon may then indicate the location of the suspected difference.

If it is determined that there is a difference between the patient's anatomy and the model, then the method 800 includes a process 812 for reapplying the segmentation function with different parameters to update the model. For example, a different parameter may be new seed points corresponding to new passageways. Such seed points may indicate constraint of presence or absence of a passage. Different parameters may indicate known lengths and diameters various passageways. If, however, it is determined that there is no substantial difference between the patient's anatomy and the model then the method includes a step 814 for continuing the operation as normal.

In some examples, it may be the case that there is a difference between the model and the sensed patient's anatomy because the patient's anatomy may be moving due to respiration. Thus, the respiration cycles may be accounted for to determine whether the difference is related to an actual difference between the patient's anatomy and the model, or if the difference is related only to movement of the airways resulting from respiration patterns.

In some examples, the probability values assigned to airways may be used to help determine if the model should be altered. For example, additional scrutiny may be applied to the candidate airways within a specific range below the threshold probability value. Because it is possible that such candidate airways correspond to actual airways, the sensor data may be combined with the probability data to determine whether a change in the model should be made. Additionally, a confidence metric may be applied to different sensing instruments. For example, different measurement apparatuses may have different levels of accuracy. Thus, data from different types of measurement apparatuses may be weighted based on an assigned confidence metric that is based on the understood accuracy of those measurement apparatuses.

In one example, the pre-operative steps may include creating a meta-model of the patient's anatomy of interest. The meta-model may be a generic, non-patient-specific model of the anatomy of interest. Then, the parameters of interest can be adjusted in real time as the instrument navigates a passageway to tune the meta-model to the actual patient. The parameters may include lengths, diameter, relative position, and orientation with respect to parent branch. Such parameters may be obtained using the various sensors and techniques described above.

In one example, little or no pre-operative segmentation may be performed. Rather, the segmentation can be done in real time during the procedure. Specifically, as the instrument navigates the passageway, it can obtain data that can then be used to perform the segmentation function and create the model during the procedure. Thus, the model is continually being developed as the instrument navigates the anatomy. In this case the path that leads to the target will also be updated adaptively as the model changes.

In some examples, instead of starting with a model of a patient's anatomy based on scanned images, a generic anatomy model may be used. In the case of navigating a lung, a generic model that represents a common human lung structure may be used. As the sensing tool of the instrument detects differences between the patient's anatomy and the generic anatomy model, the model is updated to conform to the patient's real anatomy. This may be done using the techniques described above. In some examples, this may involve having a set of planned paths and park locations. The planned paths and park locations can be based on positions where airways are likely to be found. The model can then be updated based on the data from the measurement apparatus as the catheter moves to the planned park locations along the planned paths.

In some examples, no pre-operatively obtained model is used. Specifically, the model may be constructed as the instrument begins navigating the passageway. For example, the sensing tool may be used to obtain data regarding the patient's anatomy. Such data may include the size and shape of various passageways. A model of the patient's anatomy can then be constructed in real time based on the data. The position of the instrument can then be registered or correlated with an image of the instrument within the model.

In some examples, the data obtained by various measurement systems may, optionally, be communicated to the operator of the medical instrument before updating the model. If it is determined that the model is missing a branch or passageway, the operator of the instrument may be informed and may elect to adjust the model based upon the new information or may elect to use the new information, with or without updating the model, to adjust a planned procedure. Alternatively, the data can be analyzed to automatically detect and update the preoperative or meta-model based on the presence of an additional branch or passageway that exists within the patient's actual anatomy but is not present within the model of that anatomy. Specifically, the location of the newly discovered branch can be used as a seed for the segmentation function and the segmentation function can be reapplied.

The systems and methods of this disclosure may be used for connected bronchial passageways of the lung. The systems and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a medical instrument including a sensing tool; and
a processing unit including one or more processors, wherein the processing unit is configured to:
apply a segmentation function using a first seed to a three-dimensional image of a patient anatomy to create a model;
receive position data from the medical instrument while navigating the patient anatomy;
register a position of the medical instrument with the model;
receive data related to the patient anatomy from the sensing tool; and
update the model in response to detecting a difference between the model and the patient anatomy, wherein updating the model includes reapplying the segmentation function using a second seed corresponding to a passageway of the patient anatomy that is not present within the model, and wherein detecting the difference between the model and the patient anatomy includes analyzing temporal information obtained from shape data generated by the sensing tool while the medical instrument traverses portions of the patient anatomy not represented by the model.

2. The system of claim 1, wherein the difference between the model and the patient anatomy comprises the passageway within the patient anatomy that is not present within the model.

3. The system of claim 1, wherein the sensing tool comprises at least one of: a time of flight camera, a spatial data sensor, an endoscope camera, a fluoroscopic injection system, a laser scanning device, an intravascular ultrasound device, or a biopsy tool.

4. The system of claim 1, wherein detecting the difference between the model and the patient anatomy includes analyzing at least one image obtained by the sensing tool.

5. The system of claim 1, wherein the difference between the model and the patient anatomy includes a size of a first anatomical passageway.

6. The system of claim 1, wherein detecting the difference between the model and the patient anatomy includes analyzing a shape of the medical instrument from shape data obtained by the sensing tool.

7. The system of claim 1, wherein detecting the difference between the model and the patient anatomy includes determining whether the difference is based on respiratory movement of the patient anatomy.

8. The system of claim 1, wherein the sensing tool includes a fiber optic shape sensor.

9. The system of claim 1, wherein the passageway of the patient anatomy that is not present within the model is detected using the temporal information.

10. The system of claim 1, wherein detecting the difference between the model and the patient anatomy includes analyzing spatial information obtained from shape data generated by the sensing tool while the medical instrument traverses portions of the patient anatomy not represented by the model.

11. The system of claim 10, wherein the sensing tool includes an electromagnetic sensor.

12. The system of claim 10, wherein the passageway of the patient anatomy that is not present within the model is detected using the spatial information.

13. The system of claim 1, wherein the medical instrument includes a distal end and wherein registering the position of the medical instrument with the model includes registering the distal end of the medical instrument with the model.

14. The system of claim 1, wherein applying the segmentation function to create the model includes capturing a set of scanned images of the patient anatomy.

15. The system of claim 1, wherein the three-dimensional image comprises a computed tomography scan.

16. The system of claim 1, wherein the three-dimensional image comprises a Magnetic Resonance Imaging (MRI) scan.

17. The system of claim 1, wherein updating the model comprises adding additional voxels to the model or removing voxels from the model, wherein the voxels are associated with the difference between the model and the patient anatomy.

18. The system of claim 1, wherein the processing unit is further configured to alert an operator of the medical instrument that the difference between the model and the patient anatomy is detected.

19. The system of claim 18, wherein the processing unit is further configured to receive an input from the operator, and wherein updating the model includes updating the model based on the received input from the operator.

20. The system of claim 1, wherein updating the model includes adjusting a shape of a passageway in the model, and wherein the processing unit is configured to adjust the shape of the passageway in response to determining, with the sensing tool, that a diameter of the patient anatomy is different than a corresponding diameter of the passageway in the model.

21. The system of claim 1, wherein updating the model comprises at least one of: adjusting a position of a passageway within the model, adjusting a diameter of the passageway within the model, or adding an additional passageway within the model.

22. The system of claim 1, wherein receiving the data related to the patient anatomy from the sensing tool includes receiving a three-dimensional point cloud.

23. The system of claim 22, wherein the processing unit is further configured to generate a surface representation of the patient anatomy based on the three- dimensional point cloud.

24. The system of claim 1, wherein detecting the difference between the model and the patient anatomy includes analyzing shape data obtained by the sensing tool while the sensing tool is located in the passageway of the patient anatomy that is not present within the model.

25. The system of claim 1, wherein detecting the difference between the model and the patient anatomy includes analyzing shape data obtained by the sensing tool while the sensing tool is located in a passageway of the patient anatomy that is present within the model and in the passageway of the patient anatomy that is not present within the model.

26. The system of claim 1, wherein updating the model includes updating the model with a representation of the passageway of the patient anatomy that is not present within the model based on shape data obtained by the sensing tool while the sensing tool is located in the passageway of the patient anatomy that is not present within the model.

27. The system of claim 1, wherein the sensing tool extends along a length of the medical instrument.

* * * * *